(12) United States Patent
Franceus et al.

(10) Patent No.: US 11,293,310 B1
(45) Date of Patent: Apr. 5, 2022

(54) STEAM NETWORK ASSEMBLY FOR A PLANT COMPRISING AN AMMONIA-PRODUCING UNIT AND A UREA-PRODUCING UNIT

(71) Applicant: YARA INTERNATIONAL ASA, Oslo (NO)

(72) Inventors: Danny Franceus, Moerbeke-Waas (BE); Lino Giovanni Porro, Etterbeek (BE)

(73) Assignee: YARA INTERNATIONAL ASA, Oslo (NO)

( * ) Notice: Subject to any disclaimer, the term of this patent is extended or adjusted under 35 U.S.C. 154(b) by 0 days.

(21) Appl. No.: 17/419,815

(22) PCT Filed: May 8, 2020

(86) PCT No.: PCT/EP2020/062811
§ 371 (c)(1),
(2) Date: Jun. 30, 2021

(87) PCT Pub. No.: WO2020/229328
PCT Pub. Date: Nov. 19, 2020

(30) Foreign Application Priority Data

May 10, 2019 (EP) ..................................... 19173787

(51) Int. Cl.
*F01K 7/38* (2006.01)
*C07C 273/04* (2006.01)
(Continued)

(52) U.S. Cl.
CPC .................. *F01K 7/38* (2013.01); *C01C 1/04* (2013.01); *C07C 273/04* (2013.01); *F01K 7/10* (2013.01);
(Continued)

(58) Field of Classification Search
CPC . F01K 3/242; F01K 3/245; F01K 7/10; F01K 7/12; F01K 7/14; F01K 7/34; F01K 7/38; C01C 1/04; C07C 273/04
(Continued)

(56) References Cited

U.S. PATENT DOCUMENTS

| 4,628,462 A | 12/1986 | Putman |
| 5,404,724 A | 4/1995 | Silvestri |

(Continued)

OTHER PUBLICATIONS

CN-206636608-U, Nov. 2017, Wu Zhisheng (Drawing and Abstract).*
(Continued)

*Primary Examiner* — Mark A Laurenzi
*Assistant Examiner* — Mickey France
(74) *Attorney, Agent, or Firm* — Dilworth IP, LLC

(57) ABSTRACT

A steam network assembly for a plant including an ammonia-producing unit and a urea-producing unit, including a high-pressure steam line, two medium-pressure steam lines and first and second turbines supplied with high-pressure steam by the high-pressure steam line; wherein the first turbine is a condensing-type turbine with extraction into one of the two medium-pressure steam lines, and is configured to deliver power to a syngas compressor in the ammonia-producing unit of the plant, and the second turbine is a counter-pressure type turbine with extraction connected to the two medium-pressure steam lines and is configured to deliver power to a $CO_2$ compressor in the urea-producing unit of the plant. A method to distribute high-pressure steam in a steam network assembly for a plant including an ammonia-producing unit and a urea-producing unit and a method to revamp the steam network assembly for a plant including an ammonia-producing unit and a urea-producing unit.

11 Claims, 1 Drawing Sheet

(51) Int. Cl.
   *F01K 7/12*   (2006.01)
   *C01C 1/04*   (2006.01)
   *F01K 15/00*  (2006.01)
   *F01K 7/10*   (2006.01)
   *F01K 7/34*   (2006.01)

(52) U.S. Cl.
   CPC .................. *F01K 7/12* (2013.01); *F01K 7/34* (2013.01); *F01K 15/00* (2013.01)

(58) Field of Classification Search
   USPC .......................................................... 60/648
   See application file for complete search history.

(56) References Cited

U.S. PATENT DOCUMENTS

2010/0257868 A1* 10/2010 Craze ........................ C10J 3/00
                                                             60/780
2017/0260060 A1    9/2017 Panza

OTHER PUBLICATIONS

Shashi Singh et al., "New KBR Ammonia Synthesis Loop Revamp Technology Improves Plant Energy Efficiency" Feb. 1, 2009; 8 pages.
Nitrogen + Syngas, "New plants for old", British Sulphur Publishing, London GB, No. 291; Jan. 1, 2008; pp. 30-47.
European Search Report in related EP Application No. 19173787.3; dated Oct. 31, 2019; 7 pages.
International Search Report and Written Opinion in related PCT/EP2020/062811; dated Oct. 5, 2020; 15 pages.

* cited by examiner

STEAM NETWORK ASSEMBLY FOR A PLANT COMPRISING AN AMMONIA-PRODUCING UNIT AND A UREA-PRODUCING UNIT

FIELD OF THE INVENTION

The present invention provides a steam network assembly for a plant comprising an ammonia-producing unit and a urea-producing unit. A method for distributing steam in a steam network assembly for a plant comprising an ammonia-producing unit and a urea-producing unit comprising a high-pressure steam line and two medium-pressure steam lines is also provided. Furthermore, a method to revamp the steam network assembly for a plant comprising an ammonia-producing unit and a urea-producing unit comprising a high-pressure steam line, two medium-pressure steam lines and two condensing-type turbines is provided.

BACKGROUND OF THE INVENTION

A large number of industrial machines or devices, e.g. heat exchangers, require steam to operate, so the steam network is a key component of any large industrial plant. Steam can be used to provide heat to a device or it can be transformed into mechanical power by a steam turbine. The steam turbine, in its modern version, was invented in 1884. They are widely used today in a large range of industrial plants, for example power plants. The turbines receive steam under pressure, which can be produced by a boiler or other industrial processes, as energy source and deliver mechanical power on a rotating output shaft. A turbine can for example be connected to an electrical generator to produce electricity. It may also be connected to other types of devices that require an input of mechanical work, such as compressors or pumps.

Two main types of steam turbine exist: a condensing type and a counter-pressure (or back-pressure) type. A condensing-type turbine comprises a condenser which condenses the exhaust steam to liquid water. This stage decreases the temperature and pressure of the exhaust steam and increases the amount of energy extractable from the steam by the turbine: the maximum amount of energy that can be extracted from a stream of steam is directly proportional to the difference between the inlet steam pressure and temperature and the outlet steam pressure and temperature.

A counter-pressure turbine does not expand high-pressure steam down to atmospheric or sub-atmospheric pressures. Instead, it releases process steam at a pre-defined pressure which is further directed to other devices within the plant which require steam to operate. Both types can be further equipped with an extraction outlet, allowing some steam to leave the turbine at an intermediate pressure.

Urea is the most used nitrogen-based fertilizer in the world today. It is produced by reacting ammonia with carbon dioxide. Because the synthesis of ammonia, usually from nitrogen gas from the air and natural gas, produces carbon dioxide, a urea-producing unit may re-use the carbon dioxide produced in the ammonia-producing unit, so ammonia and urea are often produced in the same plant.

A part of a traditional steam network assembly for a plant comprising an ammonia-producing unit and a urea-producing unit is depicted in FIG. 1. It comprises three steam lines carrying steam at different pressures: a high-pressure line 1 and two medium-pressure lines, 2 and 3. Line 1 contains steam at about 11 MPa; line 2 contains steam at about 3.7 MPa and line 3 at about 2.4 MPa. Two condensing-type turbines with extraction, 10 and 11, are supplied with high-pressure steam by the high-pressure line 1 and the power produced by turbine 10 is used to drive a synthesis gas (syngas) compressor in the ammonia-producing unit of the plant and the power produced by the other turbine 11 is used to drive a carbon dioxide ($CO_2$) compressor in the urea-producing unit of the plant. The syngas, which comprises carbon monoxide (CO), hydrogen gas ($H_2$), carbon dioxide and methane, is used in the ammonia-production unit to prepare a gaseous composition comprising $N_2$, $H_2$, argon and methane, which is sent to a reactor called ammonia converter to produce ammonia. The $CO_2$ gas is used in the urea synthesis: ammonia is reacted with $CO_2$ to form urea carbamate which is subsequently decomposed into urea and water. The syngas and $CO_2$ compressors are the two units requiring the most mechanical power in an ammonia and urea plant. Historically, condensing-turbines have been used to supply the necessary power to both compressors: these turbines can generate a lot of power from steam, which is easily created in a high-pressure boiler and they can also be equipped with an extraction outlet to provide process steam to the rest of the plant. Turbine 10 is connected to a condenser 20 via line 4. The turbine also comprises an extraction outlet, which is connected to line 5 and line 5 supplies steam to the medium-pressure line 2. Turbine 11 is connected to a condenser 21 via line 6 and comprises an extraction outlet, which is connected to line 7. Line 7 supplies steam to the medium-pressure line 3. Steam lines 2 and 3 deliver steam to process users 40 and 41, respectively. In this assembly, the two medium-pressure steam grids, comprising the respective lines and process users, are independent from each other. The medium-pressure steam line 2 delivers steam to the ammonia-producing unit and line 3 delivers steam to the urea-producing unit.

SUMMARY OF THE INVENTION

According to one aspect, a steam network assembly for a plant comprising an ammonia-producing unit and a urea-producing unit is provided. The steam network assembly comprises a high-pressure steam line, two medium-pressure steam lines and a first and second turbine connected to the high-pressure steam line for supplying both with high-pressure steam, wherein the first turbine supplied with high-pressure steam by the high-pressure steam line is a condensing-type turbine with extraction into one of the two medium-pressure steam lines, and is configured to deliver power to a syngas compressor in the ammonia-producing unit of the plant, and wherein the second turbine supplied with high-pressure steam by the high-pressure steam line is a counter-pressure type turbine with extraction connected to the two medium-pressure steam lines and is configured to deliver power to a $CO_2$ compressor in the urea-producing unit of the plant.

According to another aspect, a method for distributing the high-pressure steam in a steam network assembly for a plant comprising an ammonia-producing unit and a urea-producing unit is provided. The steam network assembly comprises a high-pressure steam line and two medium-pressure steam lines, and the method comprises the step of supplying high-pressure steam from a high-pressure steam line to a condensing-type turbine with extraction into one of the two medium-pressure steam lines, configured to deliver power to a syngas compressor in the ammonia-producing unit of the plant, and a counter-pressure type turbine with extraction connected to the two medium-pressure steam lines, configured to deliver power to a $CO_2$ compressor in the urea-producing unit of the plant.

According to another aspect, a method for revamping a steam network assembly for a plant comprising an ammonia-producing unit and a urea-producing unit is provided. The steam network assembly comprises a high-pressure steam line, two medium-pressure steam lines, two condensing-type turbines with extraction supplied with steam by the high-pressure steam line and two condensers, wherein one of the two condensing-type turbines is connected to one of the two condensers and to one of the two medium-pressure steam lines and the other one of the two condensing-type turbines is connected to the other one of the two condensers and the other one of the two medium-pressure steam lines, and wherein one of the two condensing-type turbines is configured to deliver power to a syngas compressor in the ammonia-producing unit of the plant and the other one of the two condensing-type turbine is configured to deliver power to a $CO_2$ compressor in the urea-producing unit of the plant. The method comprises the steps of: a) replacing the condensing-type steam turbine configured to deliver power to a $CO_2$ compressor, with a counter-pressure type turbine with extraction connected to the two medium-pressure steam lines; and b) removing the condenser connected to a steam outlet of the condensing-type turbine removed in step a).

DETAILED DESCRIPTION OF THE INVENTION

Figure 1:
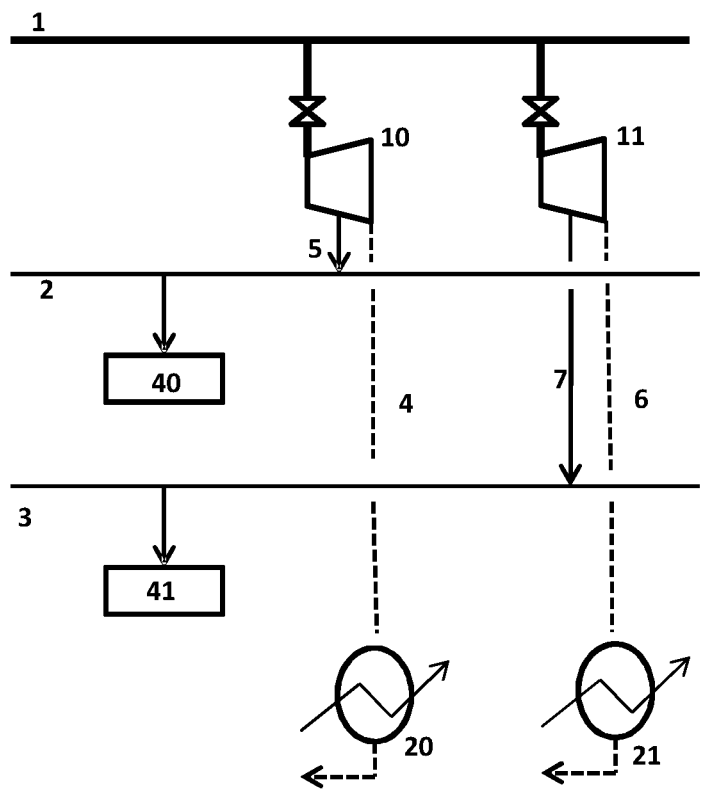
FIG. 1 represents a possible steam network assembly of an ammonia and urea plant according to common knowledge.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

All references cited in this description are hereby deemed to be incorporated in their entirety by way of reference.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

According to one aspect, a steam network assembly for a plant comprising an ammonia-producing unit and a urea-producing unit is provided. The steam network assembly comprises a high-pressure steam line, two medium-pressure steam lines and a first and second turbine connected to the high-pressure steam line for supplying both with high-pressure steam, wherein the first turbine supplied with high-pressure steam by the high-pressure steam line is a condensing-type turbine with extraction into one of the two medium-pressure steam lines, and is configured to deliver power to a syngas compressor in the ammonia-producing unit of the plant, and wherein the second turbine supplied with high-pressure steam by the high-pressure steam line is a counter-pressure type turbine with extraction connected to the two medium-pressure steam lines and is configured to deliver power to a $CO_2$ compressor in the urea-producing unit of the plant.

It was found that having a combination of a condensing-type turbine and a counter-pressure type turbine provides several advantages to the steam network assembly for a plant comprising an ammonia-producing unit and a urea-producing unit. In this combination, the counter-pressure type turbine brings advantages such as: it is cheaper than a condensing-type to install and operate, as it does not require a condenser and the relevant utilities connections (cooling water to condense the steam, pumps to evacuate the condensate, control systems, etc.) in the steam network assembly, reduced maintenance is required and it is smaller than the condensing-type, so less space is required overall for the steam network assembly. Further, the counter-pressure turbine may provide process steam to the industrial plant at more than one pressure levels. The exhaust steam from a counter-pressure turbine provides process steam at a given level, for example about 2.4 MPa. Further, the counter-pressure turbine may be installed with a steam extraction outlet that provides process steam at an intermediary pressure between the high-pressure inlet and the lower-pressure exhaust steam. In one embodiment, the counter-pressure turbine has an extraction outlet that provides steam at about 3.7 MPa. This steam can be delivered to process users present inside the same plant and requiring steam to operate. Typically, the urea-producing unit in an ammonia and urea plant requires steam at about 2.4 MPa and the ammonia-producing unit requires steam at about 3.7 MPa. On the other hand, the condensing-type turbine is able to extract more power from the high-pressure steam than a similar counter-pressure, as the pressure and temperature of the outlet steam is much lower than in a counter-pressure. It may also be equipped with an extraction outlet to supply process steam at an intermediate pressure. If both turbines, the condensing and the counter-pressure, are equipped with an extraction outlet at the same pressure, for example about 3.7 MPa, the flow of steam extracted from each turbine has to be managed depending on the steam requirement of the plant. In this configuration, the two medium-pressure steam grids become interconnected. This is usually not desirable as it complicates the running operations of a plant: if a problem occurs in the steam network in one of the units (ammonia- or urea-producing unit), it is automatically transferred into the other unit, so the control system of the steam network shall be adapted accordingly. However, it was also found that under regular operations, the overall steam consumption of the plant could be reduced. Indeed, the counter-pressure turbine may now deliver process steam at two different pressures and temperatures as required by the ammonia-producing unit and the urea-producing unit. Consequently, this reduces the amount of process steam that has to be extracted from the condensing-type turbine. If less process steam at intermediate pressure is required from the condensing turbine, a larger amount of the steam supplied to the turbine may be condensed. Thus the mass flow of steam entering the condensing turbine may be decreased while the amount of work produced by the turbine remains identical. This is possible because the efficiency of a counter-pressure turbine is usually higher than a condensing turbine: the counter-pressure turbine only operates with steam at relatively high pressure, where the lower stages of the condensing turbine operate at atmospheric or sub-atmospheric pressures. At these pressures, some of the steam is condensing in the turbine creating a liquid/gas mixture which creates frictions with the turbine blades and lowers the turbine efficiency. Within the context of this application, a turbine efficiency refers to the ability of the turbine to transform the energy from the steam into mechanical work, i.e. the ratio calculated by dividing the energy supplied by the steam entering the turbine minus the energy of the steam leaving the turbine by the amount of mechanical work produced by the turbine the energy supplied by the steam entering the turbine minus the energy of the steam leaving the turbine. The more efficient a turbine is, the less steam energy it requires to produce a given amount of work.

The steam network assembly further comprises at least two medium-pressure steam lines, each connected to at least one process user. In a plant comprising an ammonia-producing unit and a urea-producing unit, a large number of process users may require steam as an energy or heat source. Steam turbines, evaporators, strippers, condensers, heat exchangers are such process units that require steam to fulfill their tasks. Because of the multiple possible designs and applications, they may require steam with different characteristics, like pressure and temperature. It is advantageous for an industrial plant to have a steam network assembly comprising several steam lines with different pressure levels. Each line may deliver steam to process units according to their needs. A medium-pressure line may contain steam from about 2.0 MPa to about 6.0 MPa, in particular from about 3.0 MPa to about 4.0 MPa. A medium-pressure line may also contain steam from about 1.0 MPa to about 5.0 MPa, in particular from about 1.5 MPa to about 3.0 MPa. The medium-pressure steam lines may be supplied in steam by different steam producers, for example boilers or steam turbines.

Gas compressors are one of the industrial process equipment that may require a large amount of power to operate. They are used in a large variety of industrial processes and with a large array of input gases, such as natural gas, synthesis gas, ethylene, hydrogen, carbon monoxide (CO) and carbon dioxide ($CO_2$). It is common for an industrial plant to have several compressors each using different input gases. For operational purposes, it is desirable that each compressor is supplied in power by a different source, which may be a turbine.

The syngas compressor usually requires more power than the $CO_2$ compressor. It may be preferable to have the counter-pressure turbine configured to deliver power to the $CO_2$ compressor because the turbine would produce less process steam than if it was configured to deliver power to the syngas compressor. A counter-pressure turbine configured to deliver power to the syngas compressor would produce more steam than required by the plant which would be wasted and it would increase the operational costs of the plant unnecessarily.

In one embodiment, the high-pressure steam line contains steam from about 8.0 MPa to about 12.0 MPa, in particular from about 9.0 MPa to about 11.0 MPa. The energy carried by steam or energy extractable from steam by a steam turbine is related to the steam pressure and temperature. The higher the steam pressure and temperature, the more power a steam turbine can produce per amount of steam.

According to another aspect, a method for distributing the high-pressure steam in a steam network assembly for a plant comprising an ammonia-producing unit and a urea-producing unit is provided. The steam network assembly comprises a high-pressure steam line and two medium-pressure steam lines, and the method comprises the step of supplying high-pressure steam from a high-pressure steam line to a condensing-type turbine with extraction into one of the two medium-pressure steam lines, configured to deliver power to a syngas compressor in the ammonia-producing unit of the plant, and a counter-pressure type turbine with extraction connected to the two medium-pressure steam lines, configured to deliver power to a $CO_2$ compressor in the urea-producing unit of the plant.

It may be an advantage for the steam network assembly for a plant comprising an ammonia-producing unit and a urea-producing unit to comprise a high-pressure steam line that supplies steam to a condensing turbine with extraction and a counter-pressure turbine with extraction. The counter-pressure turbine produces mechanical power and process steam at intermediate pressure levels that can be used by other devices within the plant. It eliminates the need to install devices specifically to produce that steam. The condensing turbine is suitable to extract a high amount of energy from the high-pressure steam by condensing it to sub-atmospheric pressure. Surprisingly, such a steam network comprising two different types of turbines may be more efficient than a network comprising two turbines of the same type. A high-pressure steam line connected to two condensing turbines requires additional equipment (second condenser) and utilities connections raising the installation, running and maintenance costs of the network. A high-pressure steam line connected to two counter-pressure turbines would generate a lot of process steam, more than required by the plant, creating unnecessary waste. Both the counter-pressure turbine and the condensing turbine may be equipped with steam extraction outlet to obtain steam at intermediate pressure levels.

A steam network assembly is an important part of a plant comprising an ammonia-producing unit and a urea-producing unit. It comprises at least three levels (i.e. three lines with three different steam pressures): a high-pressure level (10 MPa and above), and two medium-pressure levels (each containing steam from about 2.0 to about 4.0 MPa). Steam may be generated by process equipment or boilers and distributed to various user units. The counter-pressure turbine may provide process steam to both medium-pressure steam lines. That creates an interconnection between the two grids, so the control system of the steam network shall be adapted accordingly. But, surprisingly, it was found that such an interconnection could also provide benefits to the system, such as lower overall steam usage.

According to another aspect, a method for revamping a steam network assembly for a plant comprising an ammonia-producing unit and a urea-producing unit is provided. The steam network assembly comprises a high-pressure steam line, two medium-pressure steam lines, two condensing-type turbines with extraction supplied with steam by the high-pressure steam line and two condensers, wherein one of the two condensing-type turbines is connected to one of the two condensers and to one of the two medium-pressure steam lines and the other one of the two condensing-type turbines is connected to the other one of the two condensers and the other one of the two medium-pressure steam lines, and wherein one of the two condensing-type turbines is configured to deliver power to a syngas compressor in the ammonia-producing unit of the plant and the other one of the two condensing-type turbine is configured to deliver power to a $CO_2$ compressor in the urea-producing unit of the plant. The method comprises the steps of: a) replacing the condensing-type steam turbine configured to deliver power to a $CO_2$ compressor, with a counter-pressure type turbine with extraction connected to the two medium-pressure steam lines; and b) removing the condenser connected to a steam outlet of the condensing-type turbine removed in step a).

Industrial plants are very expensive (up to several hundred million euros), so optimizing an existing plant is highly favored compared to building a new one. When the steam network assembly of a plant comprising an ammonia-producing unit and a urea-producing unit, comprises a high-pressure steam line, two medium pressure steam lines and two condensing-type turbines supplied with high-pressure steam, it may be advantageous to replace one of the two condensing-type turbines with a counter-pressure type turbine. Like any chemical process equipment, steam turbines lose their efficacy over time and need to be replaced at regular time intervals. Replacing both condensing-type turbines with counter-pressure types is not recommended because it would also generate more process steam than required by the plant, creating unnecessary waste. However, having one turbine of each type was found very advantageous since it provides a steam network assembly with advantages from both types of turbines (production of process steam from the counter-pressure type, and high power output from the condensing-type). Since a counter-pressure type turbine does not require a condenser to process one of its steam output, the condenser connected to the replaced condensing-turbine may be also removed from the steam network assembly. This also further reduces the operating and maintenance costs of the plant. Both turbines comprise at least one extraction outlet that deliver process steam at a desired pressure, which is used in the plant by various process users. The counter-pressure turbine comprises an additional extraction outlet and can deliver process steam at two different intermediate pressures, for example, 2.4 and 3.7 MPa, compared to a single pressure for the condensing turbine. One of these outlets may be at the same pressure than the extraction outlet of the remaining condensing turbine. This allows reducing the amount of steam extracted from the condensing turbine. Less input steam is subsequently required in the condensing turbine, which can condense a larger share of the input steam, and so maintains the amount of mechanical work produced. Since the efficacy of a counter-pressure turbine is generally higher than a condensing turbine, the overall amount of high-pressure steam used by both turbines may be reduced, leading to a lower operating cost of the plant.

According to another aspect, a plant, in particular a fertilizer-producing plant, comprising an ammonia-producing unit, a urea-producing unit, and a steam network assembly as described above is provided. The steam network assembly comprises a high-pressure steam line, two medium-pressure steam lines and a first and second turbine connected to the high-pressure steam line for supplying both with high-pressure steam; wherein the first turbine supplied with high-pressure steam by the high-pressure steam line is a condensing-type turbine with extraction into one of the two medium-pressure steam lines, and is configured to deliver power to a syngas compressor in the ammonia-producing unit of the plant; and wherein the second turbine supplied with high-pressure steam by the high-pressure steam line is a counter-pressure type turbine with extraction connected to the two medium-pressure steam lines and is configured to deliver power to a carbon dioxide ($CO_2$) compressor in the urea-producing unit of the plant.

Example 1

Figure 2:
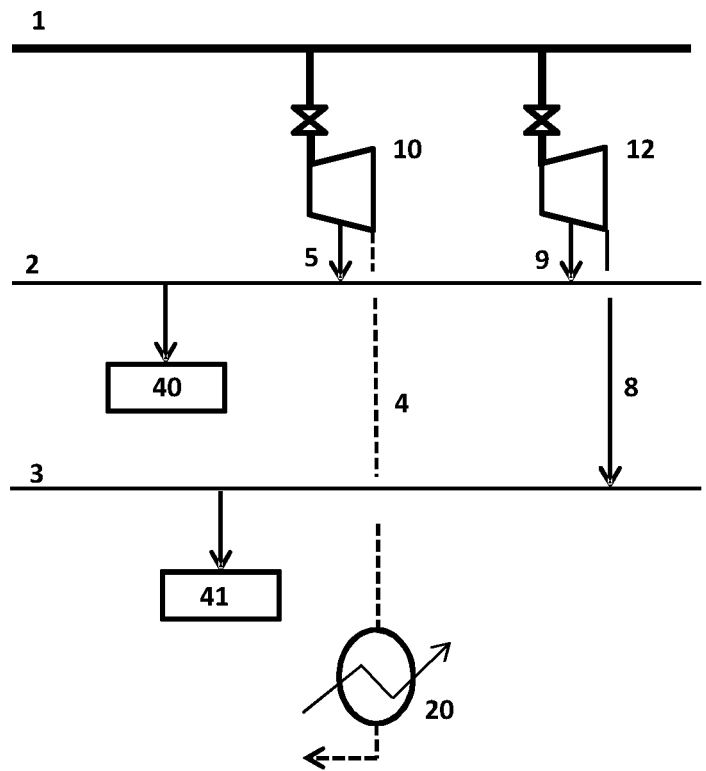
FIG. 2 represents an embodiment of a steam network assembly according to the present invention.

A steam network assembly for a plant comprising an ammonia-producing unit and a urea-producing unit according to one embodiment of the present disclosure is depicted in FIG. 2. It comprises three steam lines carrying steam at different pressures: a high pressure line 1, and two medium-pressure lines, 2 and 3. Lines 2 and 3 contain steam at about 3.7 MPa and 2.4 MPa respectively. Line 2 delivers steam to the ammonia-producing unit of the plant and line 3 delivers steam to the urea-producing unit. One condensing-type turbine with extraction 10 is supplied with high-pressure steam by the high-pressure steam line 1 and the power produced by turbine 10 is used to drive a syngas compressor. One counter-pressure type turbine with extraction 12 is supplied with high-pressure steam by the high-pressure steam line 1 and the power produced by turbine 12 is used to drive a $CO_2$ compressor. Turbine 10 is connected to a condenser 20 via line 4. It also supplies steam at 3.7 MPa to the medium-pressure line 2 via line 5. The counter-pressure turbine 12 comprises two steam outlets: one outlet is connected to line 8, it extracts steam at about 2.4 MPa and is connected to the second medium-pressure line 3. The other outlet is connected to line 9, it extracts steam at about 3.7 MPa and is connected to the medium-pressure line 2. Steam lines 2 and 3 supply medium-pressure steam, respectively, to process users 40 and 41, respectively.

The person skilled in the art realizes that the present invention by no means is limited to the embodiment described above. On the contrary, many modifications and variations are possible within the scope of the appended claims.

The invention claimed is:

1. A steam network assembly for a plant comprising an ammonia-producing unit and a urea-producing unit, comprising a high-pressure steam line, two medium-pressure steam lines and first and second turbines connected to the high-pressure steam line for supplying both with high-pressure steam;

wherein the first turbine supplied with high-pressure steam by the high-pressure steam line is a condensing-type turbine with extraction into one of the two medium-pressure steam lines, and is configured to deliver power to a syngas compressor in the ammonia-producing unit of the plant; and wherein the second turbine supplied with high-pressure steam by the high-pressure steam line is a counter-pressure type turbine with extraction connected to the two medium-pressure steam lines and is configured to deliver power to a carbon dioxide ($CO_2$) compressor in the urea-producing unit of the plant.

2. The steam network assembly according to claim 1, wherein the high-pressure steam line contains steam from about 8.0 MPa to about 12.0 MPa.

3. The steam network assembly according to claim 1, wherein one of the two medium-pressure steam lines contains steam from about 2.0 MPa to about 6.0 MPa.

4. The steam network assembly according to claim 3, wherein the other one of the two medium-pressure steam line contains steam from about 1.0 MPa to about 5.0 MPa.

5. A plant comprising an ammonia-producing unit, a urea-producing unit and a steam network assembly according to claim 1.

6. The plant according to claim 5, wherein the plant is a fertilizer-producing plant.

7. The steam network assembly according to claim 2, wherein the high-pressure steam line contains steam from about 9.0 MPa to about 11.0 MPa.

8. The steam network assembly according to claim 3, wherein the one of the two medium-pressure steam lines contains steam from about 3.0 MPa to about 4.0 MPa.

9. The steam network assembly according to claim 8, wherein the other one of the two medium-pressure steam line contains steam from about 1.5 MPa to about 3.0 MPa.

10. A method for distributing high-pressure steam in a steam network assembly for a plant comprising an ammonia-producing unit and a urea-producing unit comprising a high-pressure steam line and two medium-pressure steam lines, comprising a step of supplying high-pressure steam from the high-pressure steam line to a condensing-type turbine with extraction into one of the two medium-pressure steam lines and a counter-pressure type turbine with extraction connected to the two medium-pressure steam lines, wherein the condensing-type turbine is configured to deliver power to a syngas compressor in the ammonia-producing unit of the plant and the counter-pressure type turbine is configured to deliver power to a $CO_2$ compressor in the urea-producing unit of the plant.

11. A method for revamping a steam network assembly for a plant comprising an ammonia-producing unit and a urea-producing unit comprising a high-pressure steam line, two medium-pressure steam lines, two condensing-type turbines with extraction supplied with steam by the high-pressure steam line and two condensers, wherein one of the two condensing-type turbines is connected to one of the two condensers and to one of the two medium-pressure steam lines and the other one of the two condensing-type turbines is connected to the other one of the two condensers and the other one of the two medium-pressure steam lines, and wherein one of the two condensing-type turbines is configured to deliver output power to a syngas compressor and the other one of the two condensing-type turbines is configured to deliver power to a $CO_2$ compressor, the method comprising steps of:
   a) replacing the condensing-type steam turbine configured to deliver power to a $CO_2$ compressor with a counter-pressure type turbine with extraction connected to the two medium-pressure steam lines; and
   b) removing the condenser connected to the condensing-type turbine removed in step a).

* * * * *